United States Patent [19]

Paboojian, Jr.

[11] Patent Number: Plant 6,829

[45] Date of Patent: Jun. 6, 1989

[54] GRAPEVINE, "AMERICAN ROSE"

[76] Inventor: John Paboojian, Jr., 1005 Gleason Ave., Fowler, Calif. 93625

[21] Appl. No.: 140,777

[22] Filed: Dec. 28, 1987

[51] Int. Cl.[4] ..... A01H 5/03

[52] U.S. Cl. ..... Plt./47

[58] Field of Search ..... Plt./47

*Primary Examiner*—Robert E. Bagwill

*Attorney, Agent, or Firm*—Worrel & Worrel

[57] ABSTRACT

A new and distinct grapevine, denominated varietally as the "American Rose" which is characterized as to novelty by producing berries which have a noteworthy firm texture and which are mature for harvesting and shipment approximately September 15 to October 15 at Fowler, Calif., and which furthermore produces seeded berries which have an attractive reddish brown skin color with a greenish white halo.

1 Drawing Sheet

BACKGROUND OF THE NEW VARIETY

The present invention relates to a new and distinct variety of grapevine which will hereinafter be known as the "American Rose" and more particularly to such a grapevine which bears seeded berries, and which further is characterized principally as to novelty by a hard or otherwise extremely firm fruit texture, the subject variety being mature for commercial harvesting and shipment approximately September 15 through October 15 in the San Joaquin Valley of central California.

From a marketing standpoint, the relative times of ripening of various varieties of grapes is obviously extremely important. It has long been recognized as desirable to provide grapevines that bear fruit later than the varieties which they most nearly resemble, whereby the fruit can be brought to market at a time when competition is at a minimum. In addition, if the ripening periods of the various grapes can be spread over longer periods of time, savings and increased efficiency can be attained because the capitol outlay which is generally required to harvest and transport these grapes which are harvested within a relatively short ripening period can be spread over a longer period of time resulting in lower costs of the final product and increased uniformity of production.

The new and distinct variety of grapevine, hereinafter referred to as the "American Rose", remotely resembles in its approximate dates of harvesting, the varieties Ribier, Queen, and Emperor grapevines (all unpatented), but is distinguishable therefrom, and further characterized as to novelty by its distinctive and attractive skin coloration and further by its noteworthy leaf morphology.

ORIGIN AND ASEXUAL REPRODUCTION OF THE NEW VARIETY

The new and distinct variety of grapevine was discovered by the inventor in the mid 1970's at his ranch which is located on Manning Avenue, approximately one-half mile east of Chestnut Avenue in Fowler, Fresno County, Calif. The new variety of grapevine, which was discovered in a cultivated area as a chance seedling of uncertain parentage, was noted by the inventor at that time to have several desirable traits, and the inventor thereafter observed and evaluated it for several years prior to a full recognition of all of its numerous characteristics. The inventor, in 1984, asexually reproduced the instant grapevine by utilizing a T-budding technique and thereafter grew the resultant vines to maturity at the same ranch which is located on Manning Avenue in Fresno County, Calif. The pomological characteristics of the grapevines resulting from this first asexual reproduction have been continually observed by the inventor and it has subsequently been determined that they are identical to that of the original seedling.

BRIEF DESCRIPTION OF THE DRAWINGS

The accompanying drawing is a color photograph of a cluster of grapes of the subject variety showing their appearance sufficiently mature for harvesting and shipment; several leaves showing their dorsal and ventral coloration; a typical section of vine; and several berries halved in the axial plane to display the flesh coloration thereof, all of the instant variety.

DETAILED DESCRIPTION

Referring more specifically to the pomological details of this new and distinct variety of grapevine, the following has been observed under the ecological conditions prevailing at the ranch of the inventor which is located on Manning Avenue, approximately one-half mile east of Chestnut Avenue in Fowler, Fresno County, Calif. with due regard for cultural practices as specifically set forth hereinafter.

All major color code designations are by reference to the Dictionary of Color, by Maerz and Paul, Second Edition, published in 1950, or alternatively to the Inter-Society Color Council, National Bureau of Standards. Common color names are also used occasionally.

VINE

Size:

*Generally.*—Variable, medium to large.

Form:

*Generally.*—Upright and dense; this specific variety was trained to a quadrilateral cordon and was spur pruned. The trellis system that received the subject variety comprised a double cross-arm, with a top arm being approximately forty-two (42) inches wide and the bottom arm being approximately sixteen (16) inches wide. The trellis structure may affect the variety's characteristics inasmuch as the berries of the subject variety are somewhat susceptible to heat damage. Therefore a trellis structure which encourages the growth of a lush green canopy is conducive to the production of fruit by this grapevine variety.

Vigor: Vigorous.

Productivity: Regular, and productive; the instant variety produces one and sometimes two clusters per shoot. Current studies of the variety indicate that a mature vine would probably produce twenty-five (25) to thirty-five (35) pounds of fruit under typical central San Joaquin Valley climatic conditions.

Trunk:

*Generally.*—Large and stocky.

*Bark.*—Loose and shreddy, this bark texture is characteristic of nearly all vinifera species of grapes.

Canes:

*Size.*—Generally — average.

*Vigor.*—Average.

*Numbers.*—Medium.

*Diameter of shoots.*—Approximately 11.1 mm.

*Length of shoots.*—Variable, approximately 300 cm. to 450 cm.

*Shoots — pattern of growth.*—Straight.

*Shoots — color.*—Green when immature, the color turns somewhat reddish-brown with advancing maturity. This color is not particularly distinctive.

*Node — size.*—Enlarged.

*Nodes — length.*—Average.

*Nodes — spacing.*—Average, approximately 10.57 cm.

*Tendrils — size.*—Slender.

*Tendrils — length.*—Long.

*Tendrils — position.*—Intermittent. The variety displays a typical vinifera pattern, that is, the tendrils appear opposite two adjacent nodes, and no tendrils are present in the vicinity of each third node. The subject variety usually displays a tendril pattern wherein the first three nodes of a shoot typically are devoid of tendrils.

*Tendrils — form.*—Long, smooth, and delicate.

*Tendrils — numbers.*—Abundant.

*Tendrils — shape.*—Trifurcated, although occasionally bifurcated tendrils may be located.

Flowers:

*Generally.*—Self-fertile with upright stamens; very fruitful. The variety's flowers are average in numbers and appearance.

*Date of bloom.*—Generally — medium to late as compared with other varieties. The date of bloom in 1987 was observed on May 10, 1987. The date of bloom is approximately four to seven days after the Thompson Seedless Variety and approximately two to three days after the Emperor Variety of grapevine which has a bloom date which is considered medium to late. It should be understood that these bloom dates may vary considerably depending upon environmental conditions. Further, this date of bloom may be approximately seven to ten days early inasmuch as 1987 was considered an early year.

*Length of bloom.*—Approximately seven days.

*Color of blossoms.*—Yellow; the color is not particularly distinctive.

*Stamens.*—Length — Long.

*Filaments.*—Size — Average.

*Pollen.*—Amount — Abundant.

LEAVES

Size:

*Generally.*—Average.

*Average length.*—Approximately 12.01 cm.

*Average width.*—Approximately 12.8 cm. The instant variety of grapevine typically produces leaves which have a width dimension which is greater than the length dimension.

*Average thickness.*—Approximately 0.4 mm. The leaf thickness is considered thin as compared with other varieties.

*Sinus depressions.*—Generally — average in size.

*Petiolar sinus.*—Shape — wide and V-shaped; the petiolar sinus is open at the top and occasional overlapping is sometimes evident.

*Superior sinuses.*—Generally — average in depth; the superior sinuses generally extend approximately half-way into the leaf.

*Inferior sinuses.*—Generally — shallow in depth; the inferior sinuses generally penetrate approximately one-third of the way into the leaf.

*Superior and inferior sinuses.*—Shape — narrow.

*Lobes.*—Generally — the leaf of the subject variety typically has five lobes with the terminal lobe being obtuse.

*Color — Dorsal surface.*—Deep green, Plate 23-L-7, page 69; [125. m. 01 G].

*Color — Ventral surface.*—Light green, Plate 20-H-5, page 63; [120. m.Y G].

*Texture — ventral surface.*—Glabrous.

*Texture — dorsal surface.*—A small amount of bulging of parenchyma cells is evident between the veins. The bulging may have a smooth texture, or appear as slight bumps. This is not significant, however, and the overall leaf appearance is generally considered flat and may occasionally appear slightly concave.

*Marginal form.*—Irregular, having both pointed and convexly shaped dentations.

FRUIT

Maturity when described: Ripe for commercial harvesting and shipment. The ripening date of the subject variety can vary greatly depending not only on the climatic conditions in the San Joaquin Valley of central California but further by the type of trellis system which is employed when growing same. More particularly, climatic conditions which are characterized by substantially cool summer nights will cause the instant variety to develop its characteristic color. Moreover, a relatively wide trellis system which permits the fruit to hang freely and without congestion from the leaves and which further causes the leaves to shield or otherwise protect the fruit from the sun and the heat of the day, will encourage good color development in this variety. The anticipated ripening data of this variety during an average season is estimated to be approximately September 15 through October 15. The ripening date is considered to be medium to late as compared with other related varieties.

Storage quality: The storage quality of the subject variety has not been completely evaluated. However, fruit of the subject variety has been held in cold storage for more than one month with no substantial deleterious effects noted. However, the stems and rachis did show some signs of withering and drying which may indicate that the variety will not withstand substantially long periods of cold storage.

Shipping quality: Unknown, however, the extremely firm texture of the fruit at commercial maturity strongly indicates that the subject variety will have noteworthy shipping characteristics.

Cluster:

*Average length.*—Medium to large, approximately 27.14 cm.

*Average cluster weight.*—Medium, approximately 571.61 grams.

*Cluster shape.*—Loose, yet well filled; generally conical, narrow, and tapering. The uppermost three or four laterals are considered medium to long in length.

*Average number of clusters per vine.*—Approximately 22–27 per vine.

*Cluster ripening.*—Uneven.

*Peduncle — average length.*—Approximately 5.41 cm.

*Peduncle — thickness.*—Average.

*Pedicels.*—Average length — approximately 8.48 mm.; this is generally considered to be long when compared with other known varieties. The berries show a strong adhesion to the pedicel, and the brush typically will separate from the berry without breaking from the pedicel.

Berry:

*Generally.*—The berries of the subject variety are relatively uniform in size and shape but are somewhat susceptible to heat damage. It is important to note, therefore, that a trellis structure that will promote the growth of a canopy of lush green foliage which will protect the subject variety from the deleterious effects of the heat and sun is required.

*Size.*—Generally — large.

*Average berry length.*—Approximately 26.1 mm.

*Average berry width.*—Approximately 24.18 mm.

*Average berry weight.*—Approximately 9.19 grams.

*Average number of berries per cluster.*—Approximately 67.5, however, larger clusters may occasionally be found which have as many as 90 to 100 berries.

*Berry color.*—Generally — Variable. The color of the subject berry is somewhat inconsistent from year to year and is determined by the yearly environmental conditions and cultural practices which are noted above. Under favorable conditions the subject variety has a dominant color which is a reddish brown, more commonly referred to as Zanzibar, Plate 8-L-5; [47 d. gy. r. BR]. Moreover, the subject variety will typically have a small halo which encircles the pedicel, the halo is usually greenish-white or greenish-yellow in color, [121. p. Y G].

*Skin.*—Generally — tight.

Flesh:

*Appearance.*—Reddish white and translucent.

*Texture.*—Noteworthy, extremely firm.

*Flavor.*—Neutral, occasionally sweet. No astringency noted.

*Aroma.*—Slight.

*Juice quality.*—Poor.

*Eating quality.*—Good.

Seeds: The American Rose variety of grapevine is a seeded variety.

*Average number of seeds per berry.*—Approximately 2.9.

*Seed length.*—Approximately 7.55 mm.

*Seed width.*—Approximately 4.0 mm.

*Seed shape.*—Generally — tear drop. There appears to be a distinct morphological difference between the upper neck portion and the lower body portion of the seed.

*Adhesion to the pulp.*—The seeds of the subject variety do not adhere to the pulp and are easily removed therefrom. The seeds of the subject variety exhibit morphological characteristics which are typical of viniferous grapes.

Use: Fresh table grapes for both local and long distance markets.

Although the new variety of grapevine possesses the described characteristics as a result of the growing conditions prevailing in Fowler, Calif., it is to be understood that variations of the usual magnitude and characteristics incident to growing conditions, fertilization, pruning and pest control are to be expected.

Having thus described and illustrated my new variety of grapevine, I claim:

1. A new and distinct variety of grapevine to be denominated varietally as the "American Rose" substantially as illustrated and described and which is characterized principally as to novelty by its production of a seeded substantially reddish brown colored berry which is mature for harvesting and shipment approximately September 15 through October 15 in Fresno County, Calif., said grapevines maturing in approximately the same season as the Emperior, Ribier and Queen varieties of grapevines (all unpatented) with which it is remotely related in its date of harvesting but from which it is distinguished therefrom and characterized principally as to novelty by producing berries which have a noteworthy firm texture, good eating qualities and a large size, and which further has an attractive reddish brown skin coloration with a greenish white halo, the vines of the subject variety further producing leaves which typically have a width dimension greater than the length dimension.

* * * * *

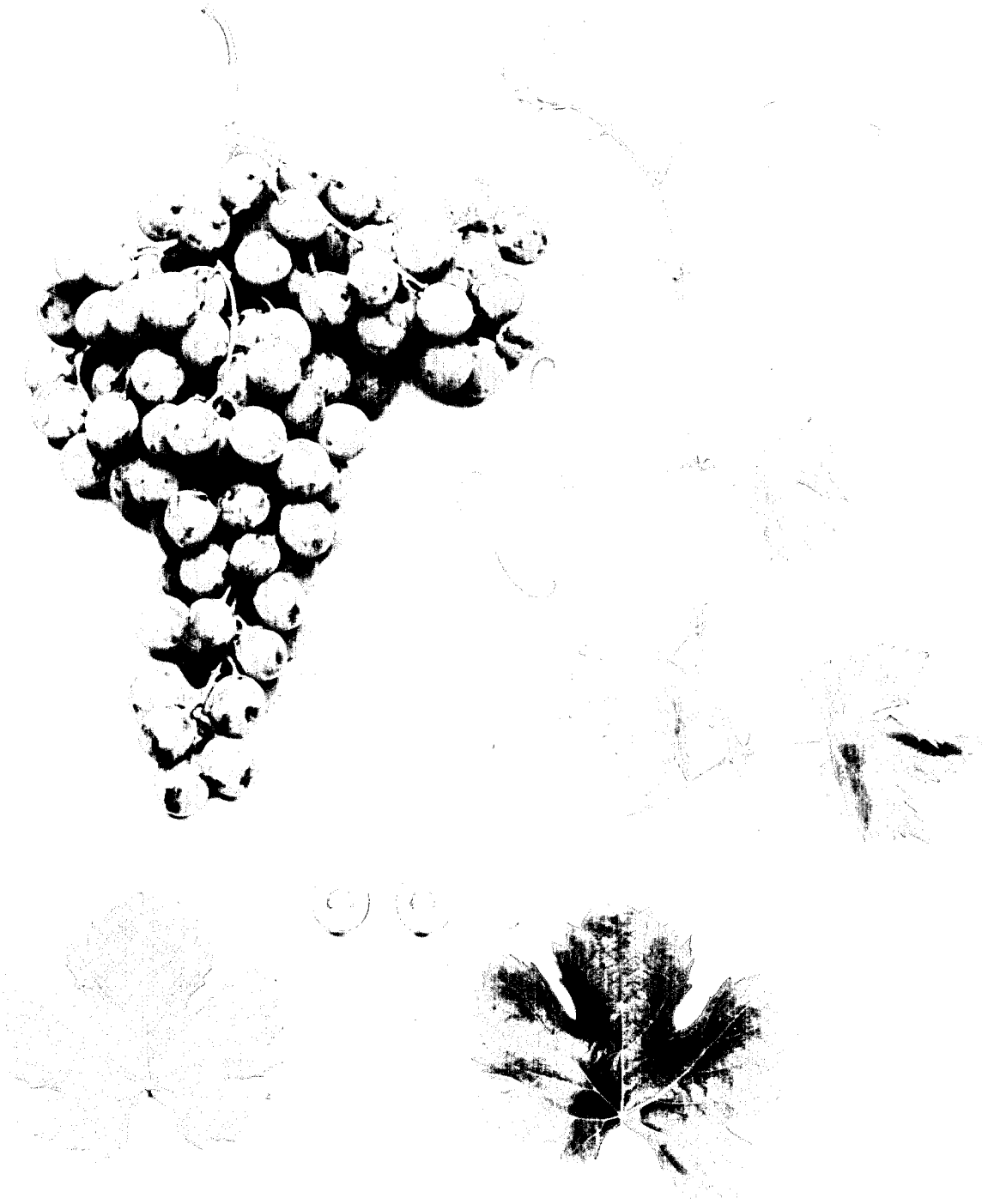

UNITED STATES PATENT AND TRADEMARK OFFICE

CERTIFICATE OF CORRECTION

PATENT NO. : PP 06,829

DATED : June 6, 1989

INVENTOR(S) : John Paboojian, Jr.

It is certified that error appears in the above-identified patent and that said Letters Patent is hereby corrected as shown below:

Column 4, Line 58

Delete "data" and Insert ---date---

Signed and Sealed this

Thirtieth Day of January, 1990

*Attest:*

JEFFREY M. SAMUELS

*Attesting Officer* *Acting Commissioner of Patents and Trademarks*